(12) United States Patent
Tu (10) Patent No.: US 6,451,011 B2
(45) Date of Patent: Sep. 17, 2002

(54) MEDICAL DEVICE HAVING TEMPERATURE SENSING AND ABLATION CAPABILITIES

(76) Inventor: Hosheng Tu, 2151 Palermo, Tustin, CA (US) 92782

( * ) Notice: Subject to any disclaimer, the term of this patent is extended or adjusted under 35 U.S.C. 154(b) by 0 days.

(21) Appl. No.: 09/827,692

(22) Filed: Apr. 7, 2001

Related U.S. Application Data (63) Continuation-in-part of application No. 09/233,418, filed on Jan. 19, 1999, now abandoned.

(51) Int. Cl.⁷ .............................................. A61B 18/18
(52) U.S. Cl. ............................ 606/21; 606/41; 128/898
(58) Field of Search .............................. 606/31, 41, 42, 606/45–50, 21–24; 607/100, 101, 102, 122

(56) References Cited

U.S. PATENT DOCUMENTS

| | | | | |
|---|---|---|---|---|
| 4,860,744 A | * | 8/1989 | Johnson et al. | ................ 606/21 |
| 5,529,067 A | | 6/1996 | Larsen et al. | |
| 5,893,885 A | * | 4/1999 | Webster, Jr. | ................. 606/31 |
| 6,113,593 A | | 9/2000 | Tu et al. | |

* cited by examiner

*Primary Examiner*—Rosiland S. Kearney (57) ABSTRACT

An ablation device system for treating tissues in a patient, the ablation device comprising capabilities for temperature sensing and providing ablation energy hyperthermically or hypothermically for treating tissue.

15 Claims, 6 Drawing Sheets

MEDICAL DEVICE HAVING TEMPERATURE SENSING AND ABLATION CAPABILITIES

RELATIONSHIP TO COPENDING APPLICATION

This application is a continuation-in-part application of Ser. No. 09/233,418 filed Jan. 19, 1999, now abandoned.

TECHNICAL FIELD OF INVENTION

The present invention generally relates to improved medical device and methods for treating tissues, and more particularly, to such a medical device and methods for treating the brain, nerve, capillary, coronary artery, tumor, atherosclerosis, or liver in a patient by delivering controlled therapeutic energy through a sensing element for treating the target tissue and sensing the tissue temperature for controlling energy therapy.

BACKGROUND OF THE INVENTION

A capillary blood vessel is one of the tube-shaped blood vessels that carry blood away from the arterioles to the body's tissues and organs. When a capillary is impaired, radiofrequency (RF) ablation therapy or cryogenic ablation therapy can be applied to the capillary to treat the tissue. To ensure proper treatment, temperature at the lesion is sensed and the temperature reading is transmitted to an external monitor for temperature monitoring and for controlling energy delivery. A conventional ablation device, for example the device disclosed by Webster, Jr. in U.S. Pat. No. 5,893,885 comprises an electrode for RF energy delivery with a temperature sensor soldered under the electrode for measuring tissue temperature. The bulky size of the conventional ablation device might pose safety concerns to a patient when it is forced into a place of a capillary. A miniaturized energy-delivery device is needed to pass into the tiny capillary opening for tissue treatment. The "ablation energy" in this invention is generally referred to either thermal energy (hyperthermic) or cryogenic energy (hypothermic).

A liver cancer or tumor is difficult to treat because of its softness and hard to reach. Ablation therapy, either hyperthermic or hypothermic, has been applied to treat the liver tissue. However, the existing ablation device can only treat the surface of the liver because of the device's bulky construction comprising at least one electrode with a temperature sensor secured under around the electrode. A miniaturized energy-delivery device is needed to reach a liver and optionally into the liver for therapeutic treatment.

Similarly, a nerve is located within a restricted space which is difficult for a bulky ablation device to get access to. A miniaturized energy-delivery device is needed to reach a nerve for therapeutic treatment.

One method of treating cellular tissues in vivo has been used in the treatment of many diseases, or as an adjunct to surgical removal procedures. This method applies appropriate heat to or withdraws heat from the tissues, and causes cell apoptosis. It can be performed on a minimally invasive fashion, which is often less traumatic than surgical procedures and may be the only alternative method, wherein other procedures are unsafe or ineffective.

In the hyperthermic therapy, RF therapeutic protocol has been proven to be highly effective when used by electrophysiologists for the treatment of tachycardia; by neurosurgeons for the treatment of Parkinson's disease; and by neurosurgeons and anesthetists for other RF procedures such as Gasserian ganglionectomy for trigeminal neuralgia and percutaneous cervical cordotomy for intractable pains. Radiofrequency treatment, which exposes a patient to minimal side effects and risks, is generally performed after first locating the tissue sites for treatment. RF energy through a temperature sensing element of the present invention, when coupled with a temperature control mechanism, can be supplied precisely to the device-to-tissue contact site to obtain the desired temperature for treating a tissue.

Another type of tissue ablation methods might include "cold therapy". Larsen et al. in U.S. Pat. No. 5,529,067 discloses methods and apparatus for use in procedures related to the electrophysiology of the heart. Specifically, Larsen et al. discloses an apparatus having thermocouple elements of different electromotive potential conductively connected at a junction, whereby an electrical current is passed through the thermocouple elements to reduce the temperature of the junction in accordance with the Peltier effect and thereby cool the contacted tissue. A detailed description of the Peltier effect and an apparatus utilizing the Peltier effect is set forth in U.S. Pat. No. 4,860,744 entitled "Thermoelectrically Controlled Heat Medical Catheter" and in U.S. Pat. No. 5,529,067 entitled "Methods For Procedures Related to the Electrophysiology of the Heart", the entire contents of both of which are incorporated by reference herein.

The above-mentioned prior art has the advantage of using the device as a treatment apparatus; however, they do not provide any means for sensing temperature and applying ablation energy using the same miniaturized non-electrode sensing element to reach the target tissue at a restricted place.

A thermocouple is a temperature sensing device consisting of a junction or joint of two dissimilar metals which has a millivolt output proportional to the difference in temperature between the "hot" junction and the lead wires (cold junction). Temperature measurements using a thermocouple are based on the discovery by Seebeck in 1821 that an electric current flows in a continuous circuit of two different metallic wires if the two junctions are at different temperatures. In electric circuits, the current is dependent on the electromotive force developed and the resistance of the circuit. For accurate temperature measurements, the measuring instrument is constructed so that a no-current electromotive force is measured to eliminate the effects of circuit resistance. The materials used for the wires typically include copper, nickel-chromium, iron, platinum, nickel-aluminum, and Constantan. A good reference for more information on thermocouples is Perry's Chemical Engineer's Handbook $6^{th}$ Edition, published by McGraw-Hill Book Company, 1973.

A thermister is a temperature-sensing device manufactured of a mixture of metal oxides. A large change in resistance is exhibited proportional to a change in temperature. Electrical conductors experience a change in resistance with temperature which can be measured with a Wheatstone-bridge circuit. The relationship for platinum reference is very exact and hence serves as a primary standard over a wide temperature range. A good reference for more information on thermister is Mark's Standard Handbook for Mechanical Engineers $8^{th}$ Edition, published by McGraw-Hill Book Company, 1978.

Thermostatic bimetal thermometers can be defined as a composite material made up of strips of two or more metals fastened together. Types of elements used in bimetal thermometers are flat spiral, single helix, and multiple helixes. This composite, because of different expansion rates of its components, tends to change curvature when subjected to a change in temperature.

One major drawback of the conventional ablation devices, either hyperthermic or hypothermic, is its bulkiness. For example, a conventional RF ablation catheter generally comprises at least one electrode with its associated temperature sensing element secured under, behind, or around the electrode. The total space needed for an electrode and its additional temperature sensing element makes the device not suitable for certain tissue ablation applications due to the tissue's restricted location or space. Therefore, there is a clinical need for an improved ablation device system having the capabilities of measuring tissue temperature, delivering therapeutic energy (hyperthermic, hypothermic or a combination thereof), and/or controlling the energy delivered for optimal effectiveness in the tissue treatment.

SUMMARY OF THE INVENTION

In general, it is an object of the present invention to provide a method and an improved ablation device system for treating the nerve, brain, capillary, liver, artery, prostate, other tissue, or atherosclerosis. It is another object of the present invention to provide a method and a device system for monitoring the temperature of the target tissue, and to control the temperature by utilizing a temperature control mechanism and/or algorithm for energy delivery. It is still another object of this invention to provide a method and an ablation device system for treating the nerve, brain, capillary, liver, artery, prostate, other tissues, or atherosclerosis in a patient by applying RF current through a temperature sensing wire to a temperature sensing element, wherein the temperature sensing element has duel functions of temperature sensing and energy delivery. It is another object of this invention to provide a method and an ablation device system for treating the nerve, brain, capillary, liver, artery, prostate, other tissues, or atherosclerosis in a patient by applying Peltier Effect principles through two temperature sensing wires having dissimilar electromotive potentials to a temperature sensing element as a joint of the two wires, wherein the temperature sensing element has duel functions of temperature sensing and cryogenic ablation therapy.

The "ablation energy" is this invention refers generally to hyperthermic energy (such as radiofrequency energy), hypothermic energy (such as cryogenic energy per Peltier effects), and a combination thereof for tissue treatment.

Briefly, heat is generated by supplying a suitable energy source to a device, such as radiofrequency, ultrasound, microwave energy, alternating current energy, or laser energy. In conventional radiofrequency applications, an electrode with its underside-secured temperature sensor constitutes as the tissue contact region for treating tissues. In the present invention, energy can be applied to the non-electrode temperature sensing element and consequently to the tissues directly without passing through an electrode of a conventional device. A DIP (dispersive indifferent pad) type pad, that contacts the patient, is connected to the Indifferent Returning Connector on the RF generator. Therefore, the RF energy delivery becomes effective when a close circuit from a RF generator through a patient and returning to the RF generator is formed. The generator should be grounded to avoid electrical interference. Heat is controlled by the power of the RF energy delivered, the delivery mode, and by the delivery duration. The standard RF energy generator means and its applications through a conventional electrode structure, to a patient are well known for those who are skilled in the art.

In a preferred embodiment, a method for treating tissue of a patient comprises sensing temperature of the tissue using a sensing element of a medical device and applying ablation energy to the tissue through said sensing element of the medical device. The ablation energy may be hyperthermic energy, hypothermic energy or a combination thereof. In one particular embodiment, the hyperthermic energy is radiofrequency energy.

The ablation device system may further comprise temperature control mechanism for receiving temperature readings from the temperature sensing element, wherein the temperature measured from the temperature sensing element is relayed to the temperature control mechanism and is adapted to effect the RF current delivery to the temperature sensing element of the ablation device system. The RF current is preferably within the range of 50 to 2,000 kHz; though it may cover from below 50 kHz to beyond 2,000 kHz.

The temperature sensing element may consist of a thermocouples type temperature probe, a thermistor type temperature probe, a bimetal thermometers type temperature probe, and the like. In a further embodiment, the temperature sensing element may be enclosed within an elongated tubular shaft, wherein the elongated tubular shaft may further comprise a fluid passageway adapted for receiving fluid from a fluid source and venting fluid out of the elongated tubular shaft. In another embodiment, a distal portion of the elongated tubular shaft is conductive and is in contact with a portion of the temperature sensing element.

In another preferred embodiment, a method for treating tissue of a patient comprises sensing temperature of the tissue using a sensing element of a medical device and applying ablation energy to the tissue through said sensing element of the medical device, wherein the temperature sensing element comprises a joint of two wires, the two wires having dissimilar electromotive potentials conductively connected at the joint. In one embodiment, the hypothermic ablation energy is provided to the joint according to Peltier effects. Furthermore, a delivery mode of the ablation energy to the sensing element is a combination of hyperthermic energy and hypothermic energy in an alternate mode or a pulsed mode.

A medical device for sensing tissue temperature and treating tissue of the present invention comprises a sensing element, wherein the sensing element comprises a joint; two wires conductively connected at the joint; and a source of radiofrequency current being connected to one of the two wires adapted for delivering radiofrequency current to the joint for tissue treatment.

In another preferred embodiment, a medical device for sensing tissue temperature and treating tissue of the present invention comprises a sensing element, wherein the sensing element comprises a joint; two wires conductively connected at the joint, wherein said two wires have dissimilar electromotive potentials; and a heat sink of thermal current being connected to said two wires according to Peltier effects and being adapted for providing cryogenic ablation therapy to the joint for tissue treatment. Alternately, the medical device may further comprise a source of radiofrequency current being connected to one of the two wires adapted for delivering radiofrequency current to the joint for the tissue treatment.

The method and medical devices of the present invention has several significant advantages over other known systems or techniques to treat the tissues located close to a restricted location. In particular, the ablation device system comprising the temperature sensing element and the ablation energy delivery capability using the same temperature sensing element results in a more effective therapeutic effect to the difficult-to-access tissues. The target tissue of the present invention may comprise, but not limited to, a brain tissue, a nerve, an artery, a liver, a prostate, an eye, a vein, a capillary vessel, a vulnerable plaque, an atherosclerotic plaque, a tumor, a cancer, and the like.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 6, what is shown is an embodiment of the medical device system, comprising a temperature sensing element for both measuring tissue temperature and delivering ablation energy, either hyperthermically or hypothermically, and a RF or heat sink source.

Figure 1:
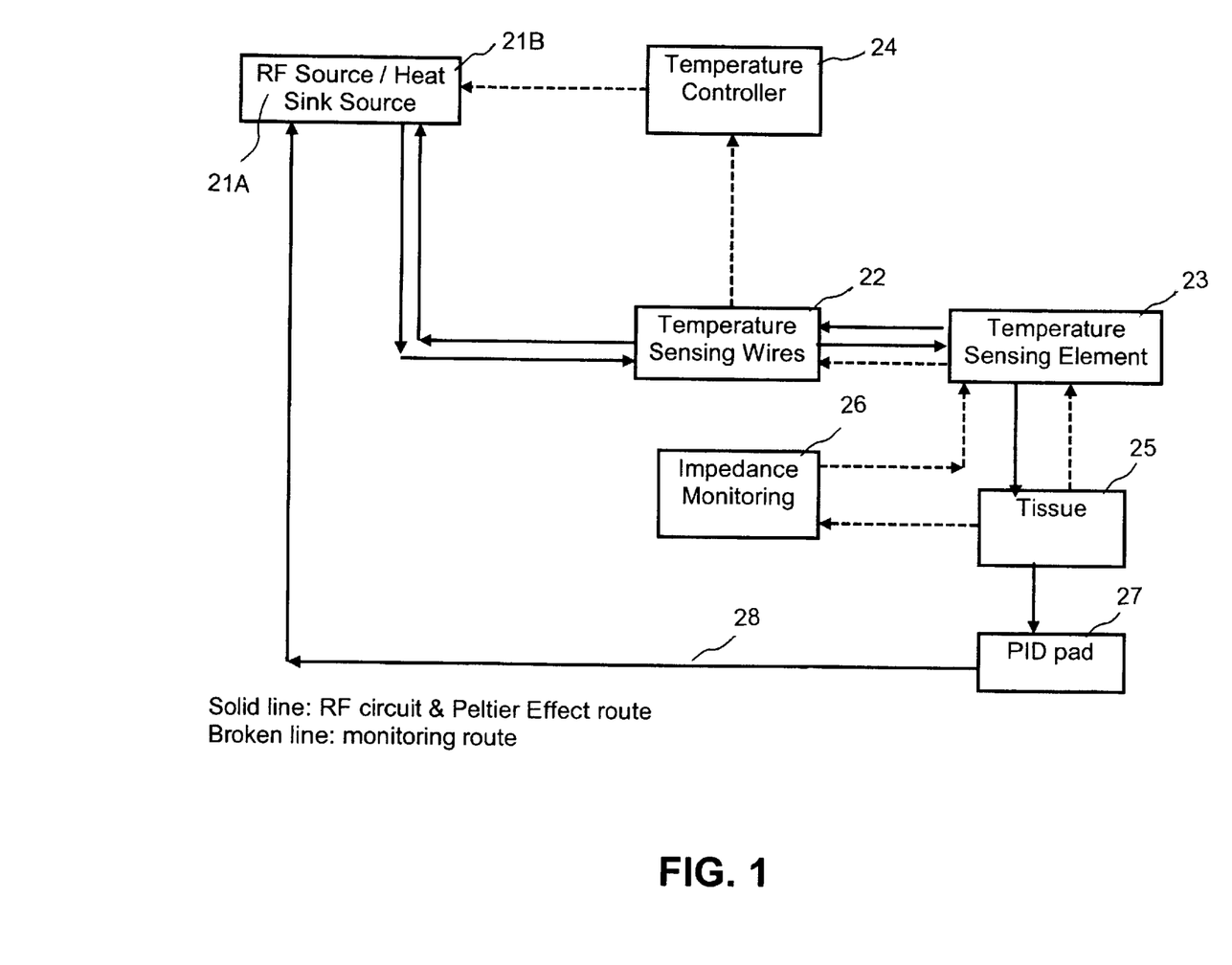
FIG. 1 is a schematic diagram of a tissue treatment method in relation to the target tissues through a temperature sensing element in a patient.

FIG. 1 shows a schematic diagram of a tissue treatment method in relation to the tissues through a temperature sensing element in a patient. A RF generator source 21A or a heat sink source 21B according to Peltier effects is connected to a temperature sensing element 23 through a temperature sensing wire or wires 22. The temperature sensing element 23 is in close contact with the underlying tissue 25 without a "conventional electrode". A "conventional electrode" is defined as a metallic unit that serves to deliver RF energy without the capability of sensing temperature. A conventional electrode along with its temperature sensing element constitutes a functional ablation unit for the prior art ablation device. An example of "a conventional electrode" is shown in U.S. Pat. No. 5,893,885. A "temperature sensing element" of the present invention is defined as a metallic joint of two wires, wherein the two wires are made of two dissimilar electromotive potentials, the joint having the capability of sensing temperature, delivering RF energy and providing cryo-ablation energy. U.S. Pat. No. 6,113,593 to Tu et al. discloses a temperature sensing element without a conventional electrode means, the entire contents of which are incorporated herein by reference.

A DIP (dispersive indifferent pad) type pad 27 that contacts the patient is connected through a connecting cable 28 to the Indifferent Returning Connector on the RF generator 21A. Therefore, the RF energy delivery becomes effective when a close circuit from a RF generator through a patient and returning to the RF generator is formed. Impedance 26 measured from the tissue contact 25 is to ensure good tissue contact for ablation therapy either hyperthermically or hypothermically, otherwise the RF source 21A or heat sink source 21B is cut off when the impedance is unreasonably high. A temperature sensing element 23 is also used to measure the tissue temperature and is relayed through temperature sensing wires 22 and a closed-loop temperature controller 24 for controlling the ablative energy delivered. Heat is controlled by the power of the RF energy delivered and by the delivery duration. The impedance and temperature monitoring routes as shown in FIG. 1 are used to assist the ablation energy operation.

Figure 2:
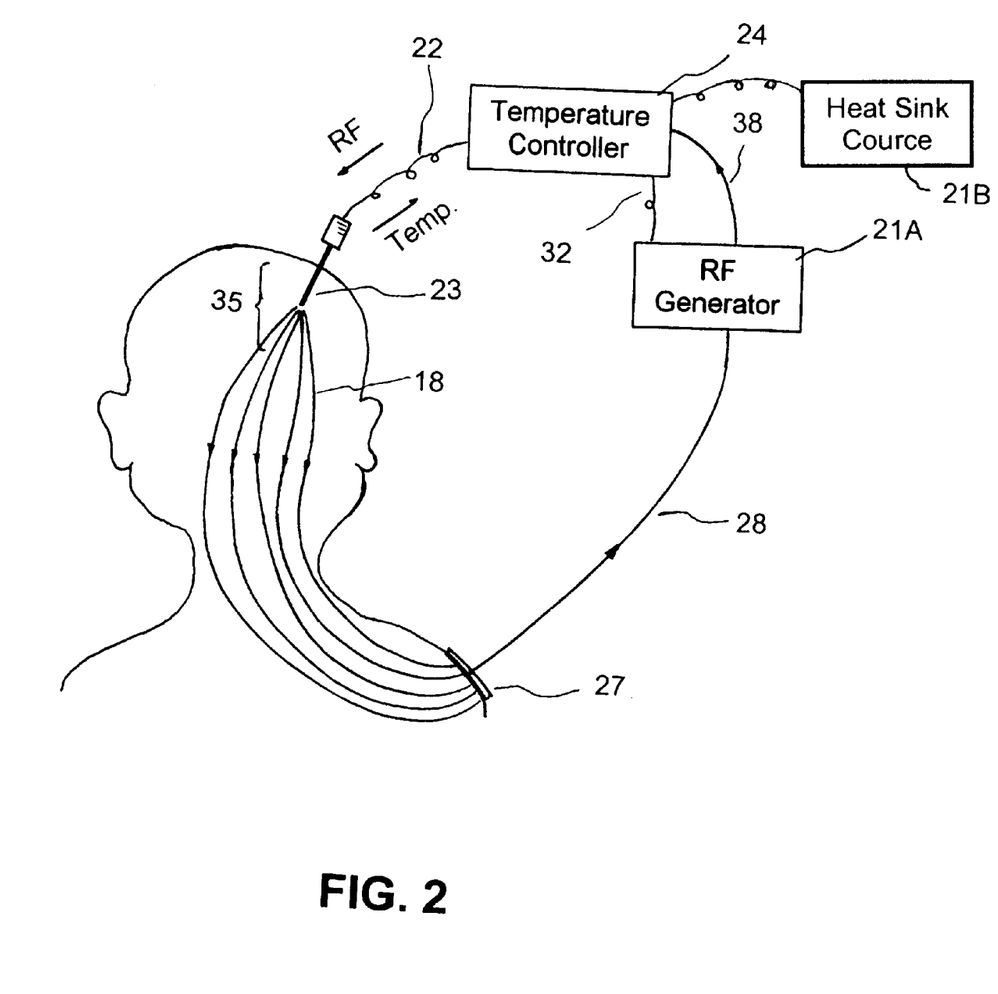
FIG. 2 is an overall view of an ablation device system in relation to the RF circuit and the cryogenic ablation of Peltier effect route, constructed in accordance to the principles of the present invention.

As shown in FIG. 2 for illustration purposes, a temperature sensing element 23 functioning as a temperature sensing plus ablation device is inserted into a brain portion 35 of a patient for tissue treatment. In one embodiment of the thermal ablation, the RF voltage for the generator 21A causes current to flow through the temperature sensing wire(s) 22, through the temperature sensing element 23, and through the patient's body 35, which is a conductive electrolytic medium. Thus, patient's body becomes part of the RF circuit. The current 18 spreads out from the temperature sensing element 23 and flows through the electrolytic tissue medium of the body. In the meantime, the temperature sensing wire 22 transmits temperature reading from the temperature sensing element 23 continuously or intermittently to a temperature controller 24 and relayed the controlling signal through a connecting medium 32 to the RF generator 21A.

In another embodiment of cryogenic ablation, the cryogenic ablation energy is provided to the temperature sensing element 23 from the heat sink source 21B according to the Peltier effect. Temperature at the sensing element 23 is continuously or intermittently measured and monitored so as to control the supply of cryogenic ablation energy.

Figure 3:
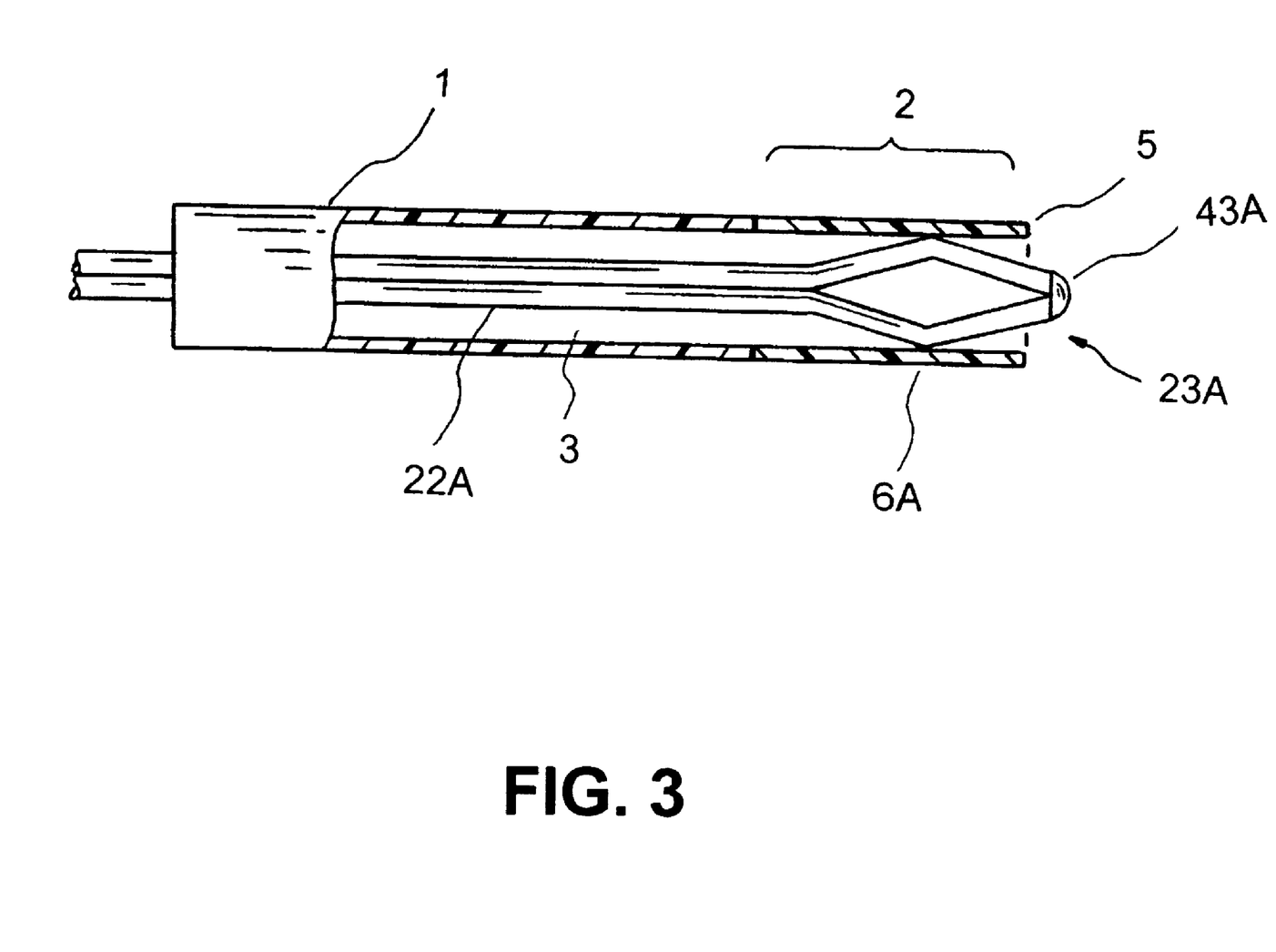
FIG. 3 is a cross-sectional view of a distal end portion of the medical device having a thermocouple sensing joint as ablation energy delivery means.

FIG. 3 shows a cross-sectional view of a distal end portion of the medical device having a thermocouples-type temperature sensing element 23A as ablation energy delivery means. In this case, the temperature sensing element 23A has a joint 43A of the two dissimilar conducting wires. In a preferred embodiment, the temperature sensing element 23A is enclosed within an elongated tubular shaft 1, having a shaft distal end 5 and a shaft lumen 3. A distal portion 2 of the elongated tubular shaft 1 may be made of conductive material and is in contact with a portion of the temperature sensing element 23A at a contact point 6A, wherein the sensing element is relayed to an external RF generator through a temperature sensing wire 22A for the thermal ablation operation. In cryogenic ablation operations, the cryo-ablation energy is provided to the joint 43A (that is, the tip of the sensing element) per Peltier effect.

Figure 4:
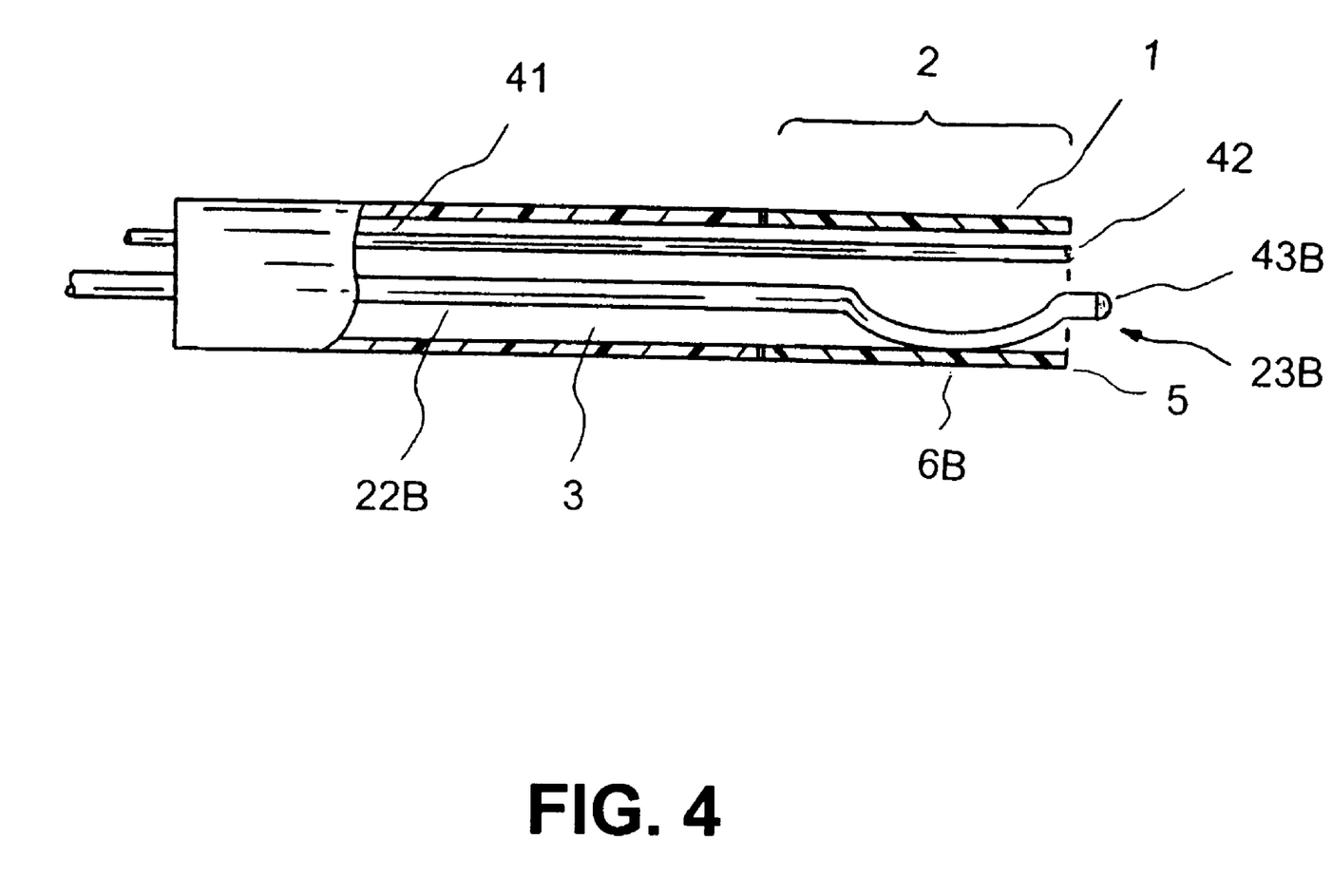
FIG. 4 is a cross-sectional view of the distal end portion of the medical device having a thermistor sensing element as RF ablation energy delivery means.

FIG. 4 shows a cross-sectional view of a distal end portion of the medical device having a thermister sensing element or bimetallic element 23B as RF ablation energy delivery means through the tip 43B. In a preferred embodiment, the temperature sensing element 23B is enclosed within an elongated tubular shaft 1, having a shaft distal end 5 and a shaft lumen 3. A distal portion 2 of the elongated tubular shaft 1 may be made of conductive material and is in contact with a portion of the temperature sensing element 23B at a contact point 6B, wherein the sensing element is relayed to an external RF generator through a temperature sensing wire 22B. The elongated tubular shaft 1 may further comprise a fluid passageway 41 adapted for receiving fluid from a fluid source and venting fluid out of the elongated tubular shaft at a distal opening 42.

Figure 5:
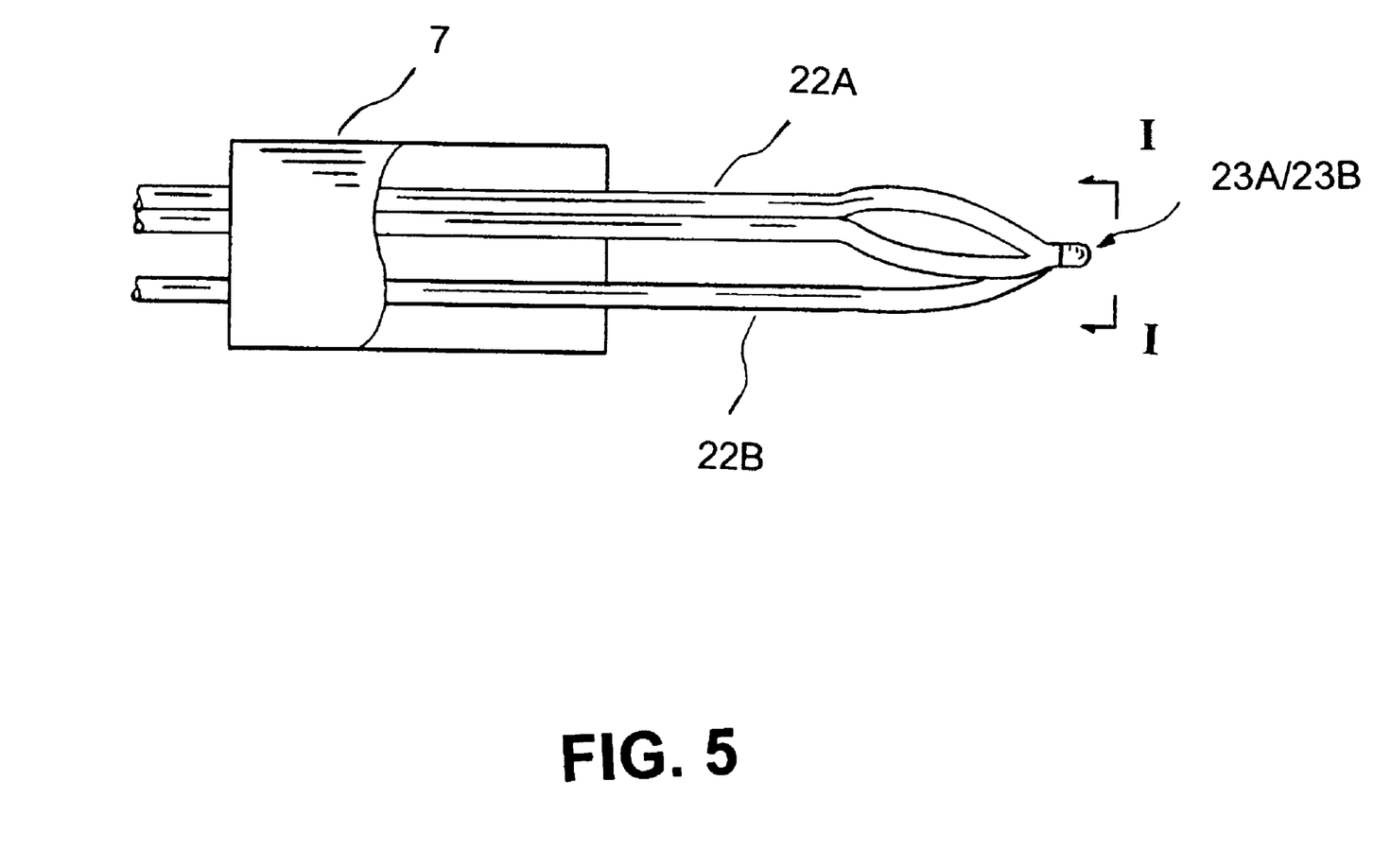
FIG. 5 is a cross-sectional view of a distal end portion of the medical device having a plurality of temperature sensing elements, wherein at least one sensing element functions as ablation energy delivery means.

FIG. 5 shows a cross-sectional view of a distal end portion of the medical device having a plurality of temperature sensing elements 23A, 23B, wherein at least one temperature sensing element functions as ablation energy delivery means. The plurality of temperature sensing elements may comprise thermocouples type, thermister type, bimetallic thermometer type or a combination thereof. In an alternate embodiment, a handle 7 may be attached to a proximal end of the temperature sensing wires 22A, 22B.

Figure 6:
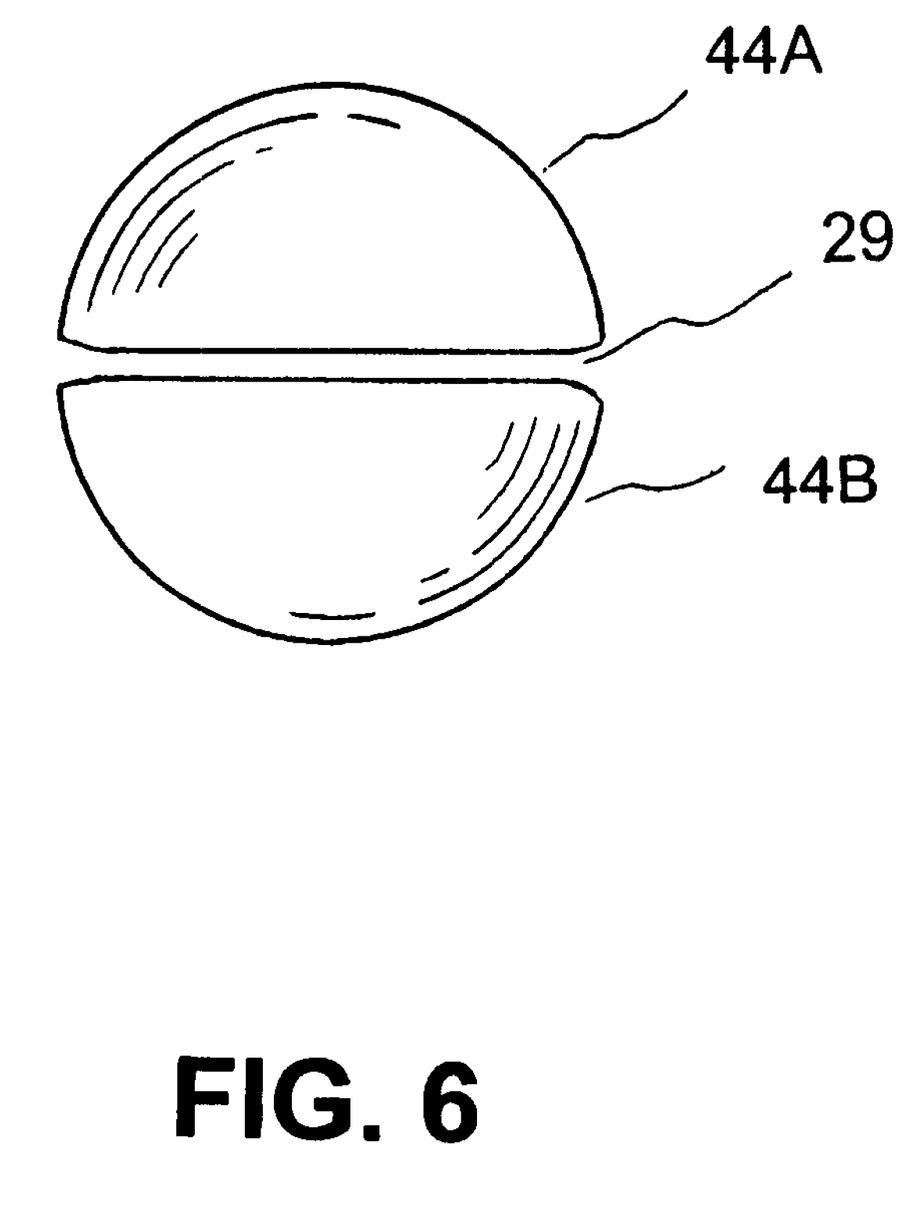
FIG. 6 is a front view of section I—I of FIG. 5, showing the distal end portion of the device having a plurality of temperature sensing element tips.

To maintain the joint of the temperature sensing element of the present invention at its minimal dimension, a semi-spherical end-unit may be constructed for the thermocouple sensing element 23A or the thermister sensing element 23B as shown in FIG. 6. FIG. 6 shows a front view of section I—I of FIG. 5, showing the distal end portion of the device having a plurality of temperature sensing element tips 44A, 44B. An insulative barrier 29 is usually placed between the two temperature sensing elements of the end-unit.

In the thermal ablation mode, the RF energy delivery is controlled by using the measured temperature from the temperature sensing element 23, through a closed-loop temperature control mechanism 24 and/or algorithm. When the measured temperature rises to a preset high-limit point, the temperature control mechanism sends out a signal to cut off the RF energy supply. In a similar manner, when the measured temperature drops to a preset low-limit point, the temperature control mechanism sends out a signal to activate the RF energy supply. The same principles apply to the cryogenic ablation mode of the present invention.

During operations, the method comprises steps of (a) inserting the temperature sensing element of the medical device of the present invention through an opening to a location of the tissue to be treated; (b) positioning the at least one temperature sensing element at the tissue to be treated; and (c) providing ablation energy through the temperature sensing wires to the at least one temperature sensing element to effect treatment of the tissue.

From the foregoing description, it should now be appreciated that an ablation medical device system for the treatment of tissues in a difficult-to-access location comprising an ablation energy source, either hyperthermically or hypothermically, through the temperature sensing wires and temperature sensing element has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for treating tissue of a patient comprising sensing temperature of said tissue using a sensing element of a medical device and applying ablation energy to said tissue through said sensing element of the medical device wherein said sensing element of the medical device comprises a joint of two wires, the two wires having dissimilar electromotive potentials conductively connected at the joint, wherein the ablation energy is cryogenic ablation energy, said cryogenic ablation energy being provided to the joint according to Peltier effects.

2. The method according to claim 1, wherein the tissue is a brain tissue.

3. The method according to claim 1, wherein the tissue is a nerve.

4. The method according to claim 1, wherein the tissue is an artery.

5. The method according to claim 1, wherein the tissue is a liver.

6. The method according to claim 1, wherein the tissue is a prostate.

7. The method according to claim 1, wherein the tissue is an eye.

8. The method according to claim 1, wherein the tissue is a vein.

9. The method according to claim 1, wherein the tissue is a capillary vessel.

10. The method according to claim 1, wherein the tissue is a vulnerable plaque.

11. The method according to claim 1, wherein the tissue is an atherosclerotic plaque.

12. The method according to claim 1, wherein the tissue is a tumor or cancer.

13. A method for treating tissue of a patient comprising sensing temperature of said tissue using a sensing element of a medical device and applying ablation energy to said tissue through said sensing element of the medical device wherein said sensing element of the medical device comprises a joint of two wires, the two wires having dissimilar electromotive potentials conductively connected at the joint, wherein a delivery mode of the ablation energy to the sensing element is a combination of hyperthermic energy and cryogenic ablation energy in an alternate mode.

14. A medical device for sensing tissue temperature and treating tissue comprising:

a sensing element, wherein the sensing element comprises a joint adapted for sensing the tissue temperature;

two wires conductively connected at the joint, wherein said two wires have dissimilar electromotive potentials; and a heat sink of thermal current being connected to said two wires according to Peltier effects and being adapted for providing cryogenic ablation therapy to the joint for tissue treatment.

15. The medical device of claim 14, the medical device further comprising a source of radiofrequency current being connected to one of said two wires adapted for delivering radiofrequency current to the joint for tissue treatment.

* * * * *